(12) United States Patent
Mizuno

(10) Patent No.: US 8,967,807 B2
(45) Date of Patent: Mar. 3, 2015

(54) OPHTHALMOLOGIC PHOTOGRAPHING APPARATUS

(71) Applicant: Nidek Co., Ltd., Gamagori-shi, Aichi (JP)

(72) Inventor: Katsuyasu Mizuno, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/905,993

(22) Filed: May 30, 2013

(65) Prior Publication Data

US 2013/0321770 A1    Dec. 5, 2013

(30) Foreign Application Priority Data

May 30, 2012    (JP) ................. 2012-122625

(51) Int. Cl.
- *A61B 3/14*    (2006.01)
- *A61B 3/10*    (2006.01)
- *A61B 3/02*    (2006.01)

(52) U.S. Cl.
USPC ............ 351/206; 351/208; 351/221; 351/243

(58) Field of Classification Search
USPC ................................ 351/200–246
See application file for complete search history.

(56) References Cited

U.S. PATENT DOCUMENTS

| | | | | |
|---|---|---|---|---|
| 7,780,292 | B2 * | 8/2010 | Kakuuchi et al. | 351/206 |
| 8,517,537 | B2 * | 8/2013 | Suehira et al. | 351/208 |
| 2003/0063258 | A1 | 4/2003 | Torii et al. | |
| 2005/0057722 | A1 | 3/2005 | Koest | |

FOREIGN PATENT DOCUMENTS

| | | |
|---|---|---|
| JP | 3013356 B | 12/1999 |
| JP | 2005-87729 A | 7/2005 |

OTHER PUBLICATIONS

Extended European Search Report dated Sep. 5, 2013 filed in corresponding EP application No. 13169727.8.

* cited by examiner

*Primary Examiner* — Mohammed Hasan
(74) *Attorney, Agent, or Firm* — Rankin, Hill & Clark LLP

(57) ABSTRACT

An ophthalmologic photographing apparatus includes: an illuminating optical system for irradiating an examinee's eye with illuminating light; an imaging optical system including an imaging device for receiving a reflected light flux from the eye, the imaging optical system having an imaging optical axis inclined with respect to an optical axis of the illuminating optical system; and a first optical member for reducing an imaging incidence angle, the imaging incidence angle being defined as an angle between a normal direction of an imaging surface of the imaging device and a principal ray of the reflected light flux.

16 Claims, 5 Drawing Sheets

OPHTHALMOLOGIC PHOTOGRAPHING APPARATUS

CROSS-REFERENCE TO RELATED APPLICATION

This application is based on Japanese Patent Application No. 2012-122625 filed with the Japan Patent Office on May 30, 2012, the entire content of which is hereby incorporated by reference.

BACKGROUND

1. Technical Field

The present disclosure relates to an ophthalmologic photographing apparatus that photographs an examinee's eye.

2. Related Art

As an ophthalmologic photographing apparatus, for example, an apparatus including an optical system using the Scheimpflug principle is known.

For example, in a first related art (see, for example, JP-A-2005-87729), the imaging surface of an imaging device is inclined with respect to the optical axis of a lens to form a cross-sectional image of an eyeball on the imaging device. The validity of this incline is explained by the Scheimpflug principle. This incline allows light from the anterior segment to be incident on the imaging surface while being greatly inclined with respect thereto.

In a second related art (see, for example, Japanese Patent No. 3013356, the imaging surface of an imaging device is perpendicular to the optical axis. An imaging lens is inclined with respect to the optical axis. The validity of the incline of this imaging lens is also explained by the Scheimpflug principle.

SUMMARY

An ophthalmologic photographing apparatus includes: an illuminating optical system for irradiating an examinee's eye with illuminating light; an imaging optical system including an imaging device for receiving a reflected light flux from the eye, the imaging optical system having an imaging optical axis inclined with respect to an optical axis of the illuminating optical system; and a first optical member for reducing an imaging incidence angle, the imaging incidence angle being defined as an angle between a normal direction of an imaging surface of the imaging device and a principal ray of the reflected light flux.

DETAILED DESCRIPTION

Figure 1:
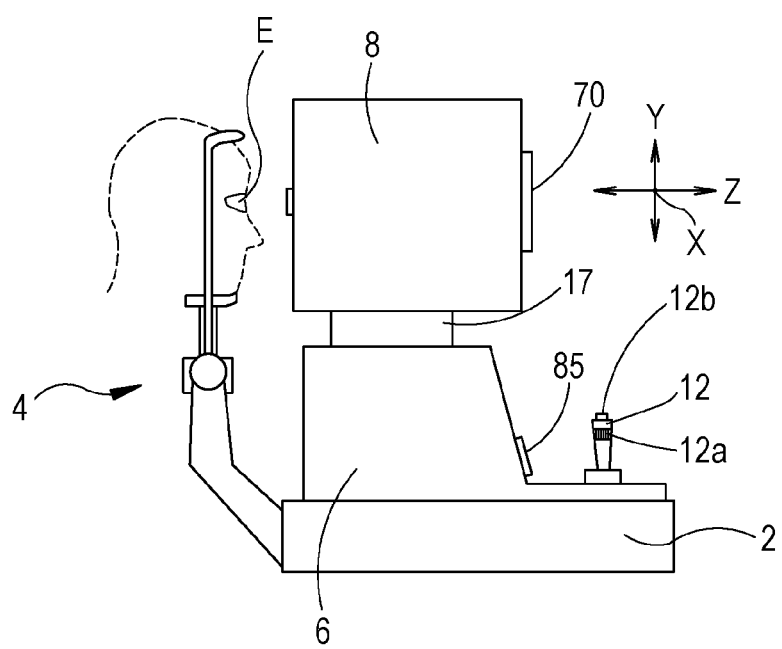
FIG. 1 is an exterior view of an anterior segment photographing apparatus according to an example of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the first related art, the sensitivity of the imaging device decreases with an increase in the incidence angle. Hence, exposure time or the amount of illumination light increases.

In the second related art, the incline of the imaging surface with respect to the optical axis is small. Hence, the sensitivity of the imaging device is hard to reduce. However, an aberration occurs due to the incline of the imaging lens with respect to the optical axis. The aperture of the imaging lens is closed down to suppress the aberration. As a consequence, exposure time or the amount of illumination light increases.

An increase in exposure time causes the prolongation of photographing time, and the prolonged time forces an examinee to continue to fixate a fixation target all that time. Furthermore, an increase in the amount of illuminating light increases the burden on the examinee.

An object of the present disclosure is to provide an ophthalmologic photographing apparatus that can reduce the burden on an examinee.

An ophthalmologic photographing apparatus includes an illuminating optical system for irradiating an examinee's eye with illuminating light; an imaging optical system including an imaging device for receiving a reflected light flux from the eye, the imaging optical system having an imaging optical axis inclined with respect to an optical axis of the illuminating optical system; and a first optical member for reducing an imaging incidence angle, the imaging incidence angle being defined as an angle between a normal direction of an imaging surface of the imaging device and a principal ray of the reflected light flux.

According to the ophthalmologic photographing apparatus, the burden on an examinee can be reduced.

A description will be given of an anterior segment photographing apparatus (the present apparatus) according to an embodiment of the present disclosure, based on the drawings. FIGS. 1 to 6 are diagrams relating to an example of the present apparatus.

<Outline>

An optical axis of an imaging optical system in the present apparatus is inclined with respect to and intersects with an optical axis of an illuminating optical system. Furthermore, the present apparatus is designed to shift an image plane (that is, the angle of the image plane) formed by the imaging optical system to bring the direction of the image plane close to perpendicular to the imaging optical axis. Consequently, the present apparatus can obtain, for example, a captured image having excellent contrast. Furthermore, in the present apparatus, image acquisition time can be reduced.

The present apparatus includes an illuminating optical system 20 and an imaging optical system 30. The present apparatus is used to photograph an anterior segment image of an examinee's eye (see FIGS. 2 and 3).

The illuminating optical system 20 irradiates an examinee's eye with illuminating light. The illuminating optical system 20 may be, for example, a slit illuminating optical system (slit illuminating system). In this case, light coming out from a light source is irradiated to (projected on) the examinee's eye as slit light. In this case, the illuminating optical system 20 includes at least a light source 21, a slit 23, and a projection lens 26. In the illuminating optical system 20, a light section (slit image) of the slit 23 is formed by illuminating the slit 23 by the light source 21. The slit image is projected (formed) on the anterior segment via the projection lens 26.

The light source 21 may be a visible light source or an infrared light source. In an example to be described later, the light source 21 emits blue light. The slit 23 includes a slit opening. Alternatively, for example, the slit 23 may be a slit plate including the slit opening. The slit 23 is arranged at a position substantially conjugated with the anterior segment. The projection lens 26 focuses a slit image formed by the slit 23 onto the anterior segment.

The imaging optical system 30 captures an image of the examinee's eye illuminated by the illuminating light. The imaging optical system 30 includes an imaging device 35 that receives a reflected light flux from the eye. In the imaging optical system 30, the imaging device 35 captures, for example, a slit cross-sectional image formed by the slit light being reflected by the anterior segment as an image of the examinee's eye. In the imaging optical system 30, a lens system forms the slit cross-sectional image on the imaging device 35. The imaging optical system 30 has an imaging optical axis L2. The imaging optical axis L2 is inclined with respect to an illumination optical axis L1 of the illuminating optical system 20.

For example, the imaging optical system 30 includes at least an imaging lens (image forming lens) 33 and the imaging device 35. For example, a two-dimensional imaging device or a one-dimensional imaging device is used as the imaging device 35. In the imaging optical system 30, the imaging device 35 captures the slit cross-sectional image on the anterior segment via the imaging lens 33. The imaging lens 33 is arranged such that its lens optical axis substantially coincides with the optical axis of the imaging optical axis L2. The lens optical axis of the imaging lens 33 may form the imaging optical axis L2. The imaging lens 33 may include a plurality of lenses. Moreover, the imaging lens 33 may serve as an objective lens arranged obliquely with respect to a visual axis.

A description will be given of another example of the illuminating optical system 20 and the imaging optical system 30. The illuminating optical system 20 may include an optical scanning system that scans the examinee's eye with laser light at high speeds in the transverse direction. In this case, the imaging optical system 30 captures a light scattering image of the examinee's eye formed by laser scanning, by the imaging device.

As another example, the illuminating optical system 20 and the imaging optical system 30 may have a structure as in a specular microscope (a corneal endothelial cell photographing apparatus). In this case, the illuminating optical system 20 irradiates the cornea with light from an oblique direction, for example. The imaging optical system 30 receives reflected light specularly reflected by the cornea, for example.

<Reduction in Incidence Angle>

An optical path of the imaging optical system 30 is provided with an optical member for reducing an incidence angle θ of a principal ray of the reflected light flux with respect to an imaging surface of the imaging device 35. An example of such an optical member is a first optical member 36. The first optical member 36 shifts an image plane (or the angle of the image plane) of an image formed by the imaging optical system 30 to bring the direction of the image plane with respect to the imaging optical axis L2 close to the perpendicular. The first optical member 36 is preferably arranged between the lens system and the imaging device 35.

Figure 4:
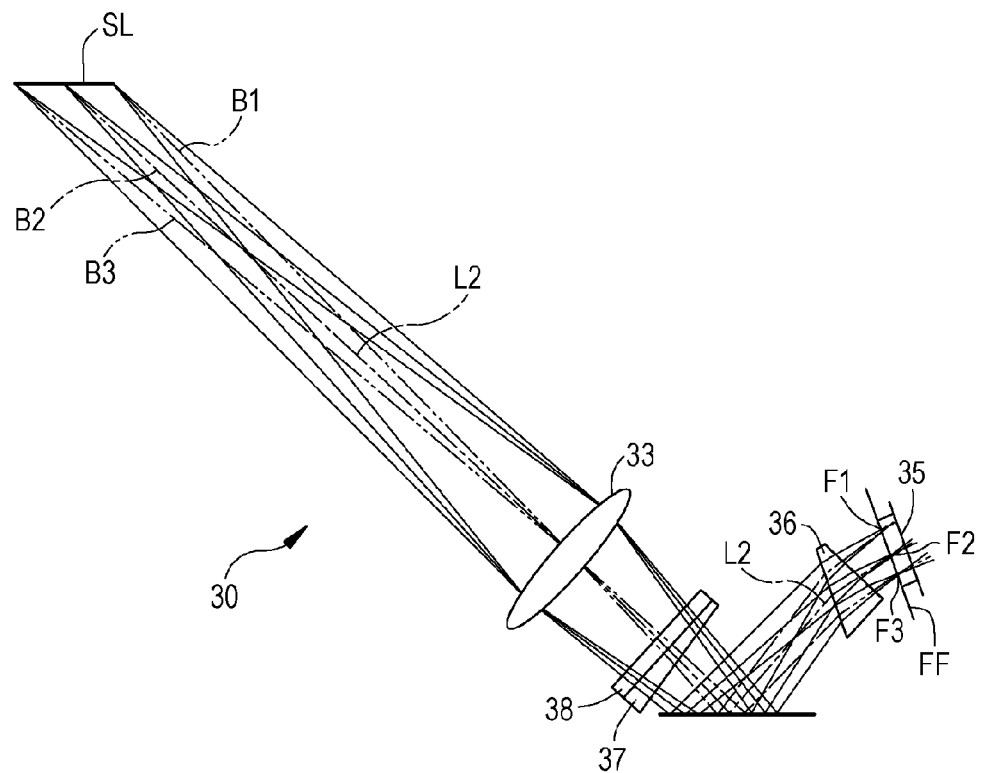
FIG. 4 is a diagram illustrating a first example of a first optical member of the anterior segment photographing apparatus.
Figure 5:
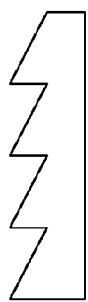
FIG. 5 is a diagram illustrating a second example of the first optical member of the anterior segment photographing apparatus.

The first optical member 36 refracts the reflected light flux from the eye, and refracts the imaging optical axis L2 (see FIGS. 4 and 5). Therefore, the first optical member 36 may be, for example, an optical member including a front surface and a back surface that intersect with each other at an acute angle. Specifically, the first optical member 36 may be an optical member having a thickness that changes continuously. In other words, the first optical member 36 may be, for example, a first deviation angle prism as illustrated in FIG. 4. The shape of the first deviation angle prism may be a wedge shape.

Moreover, the first optical member 36 may be an optical member having a thickness that changes in stages. In other words, the first optical member 36 may be a Fresnel prism as illustrated in FIG. 5. A material of the first optical member 36 may be an optical material having a higher refractive index than air and optical transparency, such as glass or plastic.

In the imaging optical system 30, the angle between an image plane FF of light from a slit cross-section SL and an optical axis of a principal ray of light from the slit cross-section SL is determined by the Scheimpflug principle.

Moreover, the imaging surface of the imaging device 35 is arranged to be parallel with the image plane FF of the light from the slit cross-section SL. Consequently, a cross-sectional image that is in focus with respect to a depth direction is captured.

With regard to this, the first optical member 36 refracts the principal rays of the light from the slit cross-section SL. The principal rays are illustrated by the chain double dashed lines in FIG. 4, and includes also a principal ray corresponding to the imaging optical axis L2. With the refraction, the image plane FF (that is, the angle of the image plane FF) shifts to bring the direction of the image plane FF with respect to the optical axis L2 close to the perpendicular. In other words, the direction of the optical axis L2 of the principal ray of the light from the slit cross-section SL toward the imaging device 35 comes close to the perpendicular to the image plane FF (that is, the imaging surface of the imaging device 35). In this manner, in the present apparatus, the imaging surface of the imaging device 35 is shifted from a position following the Scheimpflug principle as a function of a reduction in the imaging incidence angle by the first optical member 36.

Therefore, according to the embodiment, the amount of light incident on the imaging device 35 can be increased compared with a known Scheimpflug optical system. Consequently, only a short exposure time or small amount of illuminating light is necessary. Hence, the burden on the examinee can be reduced.

For example, the imaging device 35 is preferably arranged such that an angle (imaging incidence angle) formed by the normal direction of the imaging surface of the imaging device 35 and the principal ray (the optical axis of the principal ray) is 25° or less. Consequently, a reduction in the sensitivity of the imaging device 35 can be suppressed or avoided. The imaging device 35 is more preferably arranged such that the imaging incidence angle is 20° or less. Consequently, a reduction in the sensitivity of the imaging device can be further suppressed or avoided. According to an experiment of the inventor, it was found that the luminance of a captured image increases significantly by setting the imaging incidence angle to 20° or less.

<Photographing of Cross-Sectional Images at Plurality of Angles>

The present apparatus that photographs an anterior segment cross-sectional image may have a configuration for photographing anterior segment cross-sectional images at a plurality of positions. In a case of photographing a plurality of cross-sectional images, the total photographing time is the time corresponding to the number of photographed images. In the present apparatus, as described above, only a short exposure time or small amount of illumination light is necessary in photographing. Hence, the total photographing time can be reduced. As a consequence, the burden on the examinee's eye can be significantly reduced. Moreover, the instability of fixation caused by the prolongation of the photographing time can be suppressed or avoided. As a consequence, a plurality of cross-sectional images can be stably acquired.

For example, in present the apparatus, a rotation drive mechanism 100 is arranged. The rotation drive mechanism 100 rotates the illuminating optical system 20 and the imaging optical system 30 around the illuminating optical axis. While they are being rotated by 180 degrees, photographing is executed; accordingly, a cross-sectional image of the examinee's eye in each meridian direction is obtained. The rotation drive mechanism 100 includes a drive unit 101 (e.g., a pulse motor) as a driving source. The rotation drive mechanism 100 may be a rotation drive mechanism described in JP-A-2012-55333, for example.

The members of the imaging optical system 30 in the embodiment are basically arranged in accordance with the Scheimpflug principle. However, the arrangement of the imaging device 35 is set not only by the Scheimpflug principle, but also considering refraction by the first optical member 36.

<Aberration Correction Member Corresponding to First Optical Member 36>

A disadvantage of the arrangement of the first optical member 36 is that there is a possibility that coma and astigmatism, which deteriorate image quality in the center of an image, may occur. Accordingly, the imaging optical system 30 includes a configuration for correcting an aberration caused by the first optical member 36 (an aberration correction member). For example, the aberration correction member may be at least any of a deviation angle prism, a Fresnel prism, and a cylindrical lens. The aberration correction member can be advantageously arranged between the lens system and the imaging device.

A first example of the aberration correction member is a second deviation angle prism 37 arranged on the optical path of the imaging optical system 30. The second deviation angle prism 37 is used to correct coma and astigmatism caused by the first optical member 36. The second deviation angle prism 37 has a deviation angle direction opposite to the first optical member 36. The second deviation angle prism 37 can be advantageously arranged between the imaging lens 33 and the first optical member 36. This is because the light flux diameter at the second deviation angle prism 37 is larger than the light flux diameter at the first optical member 36. Hence, an aberration can be corrected by a little prism deviation angle in an opposite direction by the second deviation angle prism 37. The second deviation angle prism 37 may be a Fresnel prism.

A second example of the aberration correction member is a cylindrical lens 38 arranged on the optical path of the imaging optical system 30. The cylindrical lens 38 is used to correct astigmatism caused by the first optical member 36. The cylindrical lens 38 can be advantageously arranged between the imaging lens 33 and the first optical member 36. This is because the light flux diameter at the cylindrical lens 38 is larger than the light flux diameter at the first optical member 36. Hence, a little cylindrical refractive power in an opposite direction of the cylindrical lens 38 can correct an aberration.

Moreover, the cylindrical lens 38 can be advantageously arranged closer to the second deviation angle prism 37 than the first optical member 36.

The imaging optical system 30 does not need to include the cylindrical lens 38, depending on the setting condition. In this case, the second deviation angle prism 37 corrects coma and astigmatism. The setting conditions include, for example, the target value of the imaging incidence angle, and the minimum value of clearance between the first optical member 36 and the imaging device 35.

EXAMPLE

A description will hereinafter be given of an example of the present apparatus based on the drawings. FIG. 1 is an exterior view of the present apparatus. The present apparatus includes a base 2, a face support unit 4 mounted on the base 2, a moving platform 6 provided movably on the base 2, a measuring unit (apparatus main body) 8. The measuring unit 8 is provided movably to the moving platform 6, and houses an optical system to be described later. Moreover, the measuring unit 8 is provided with a monitor 70. The monitor 70 displays various pieces of information such as an observation image of an examinee's eye E or a measurement result.

The moving platform 6 is moved by the operation of a joystick 12 in a left and right direction (X direction) and a front and back direction (Z direction) on the base 2. Moreover, the measuring unit 8 is moved by a drive mechanism (e.g., a motor) 17 in an up and down direction (Y direction) in accordance with rotation operation on a rotating knob 12a. The moving platform 6 is provided with an operating unit 85 where switches to perform various settings are arranged. The drive mechanism 17 moves the measuring unit 8 in the X, Y, and Z directions with respect to the examinee's eye. The present apparatus may or may not include a mechanical sliding mechanism for moving the moving platform 6. The present apparatus may be configured such that the drive mechanism 17 moves the measuring unit 8 more widely than the pupillary distance.

Figure 2:
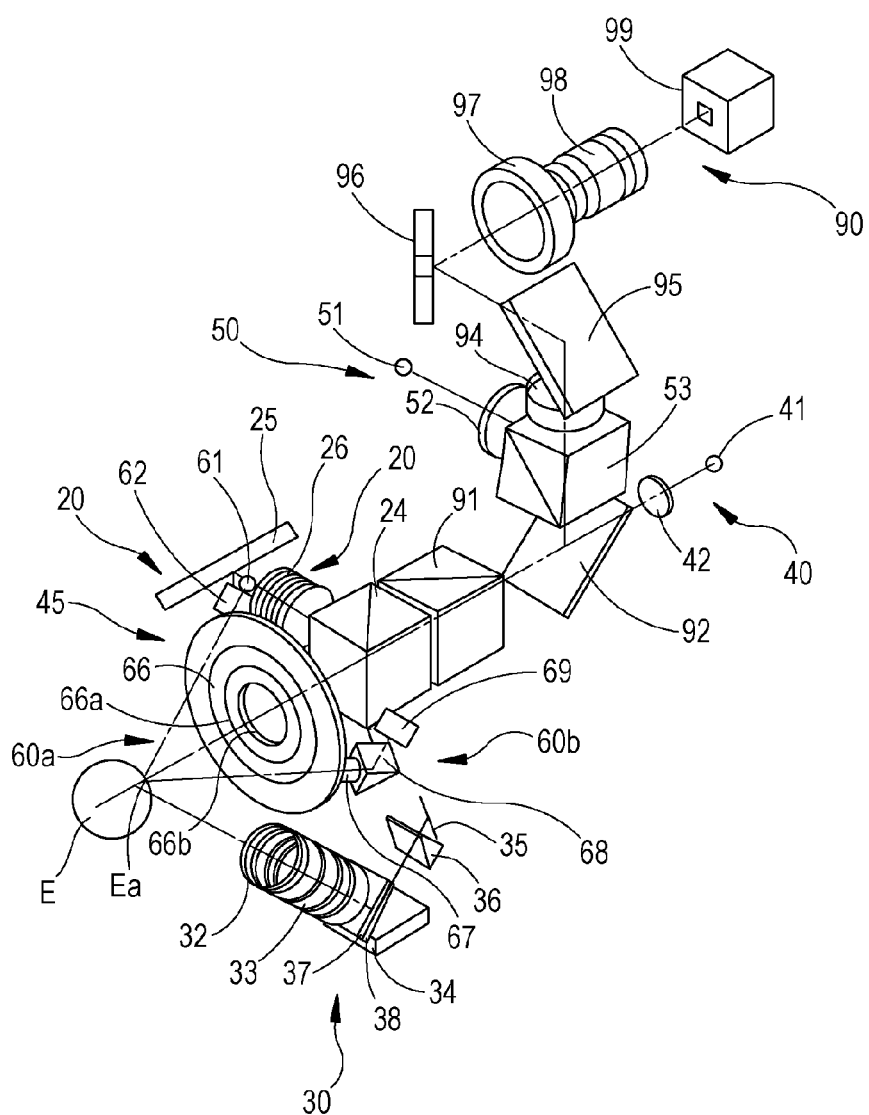
FIG. 2 is a perspective view of an optical system of the anterior segment photographing apparatus.
Figure 3:
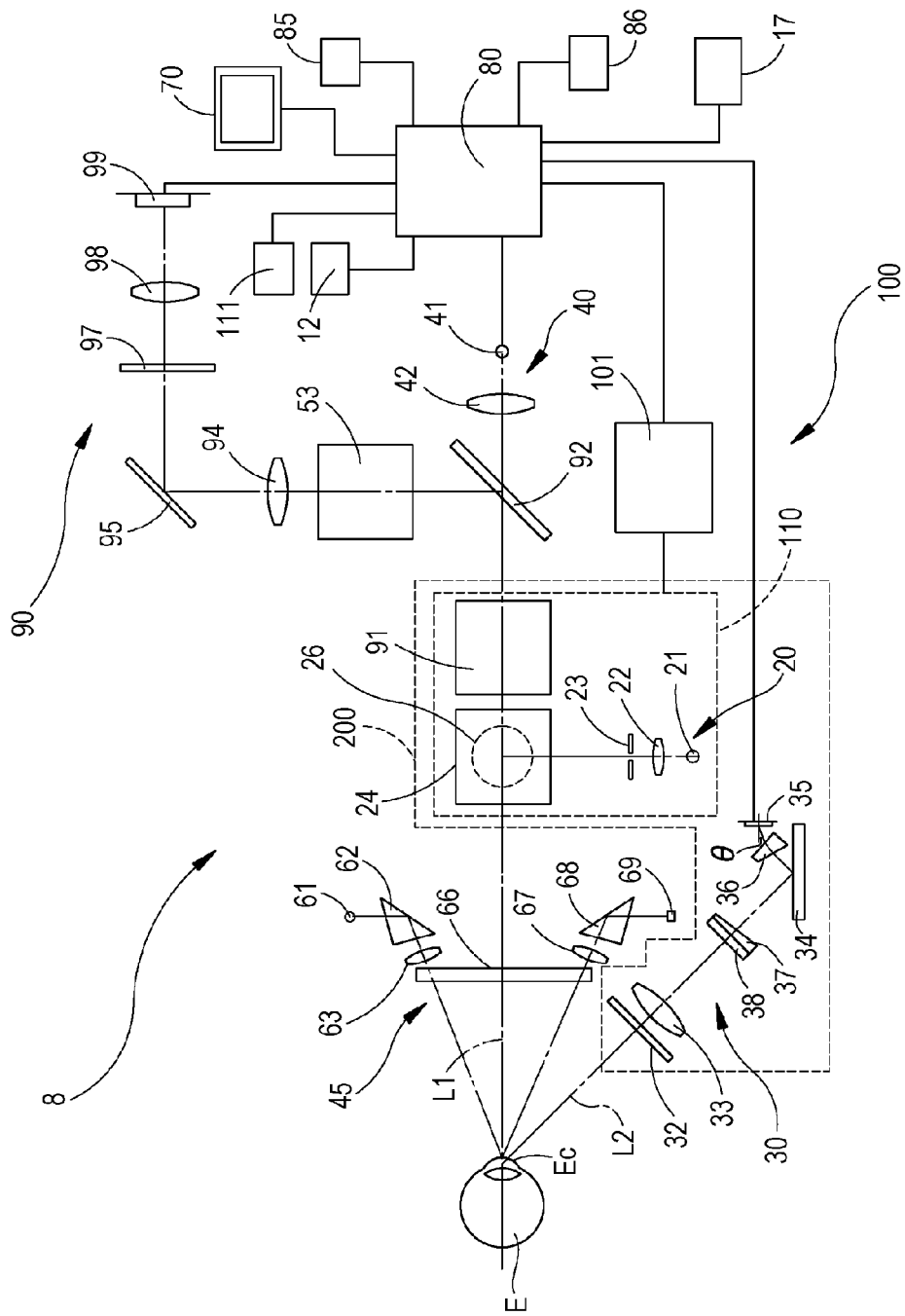
FIG. 3 is a side view of the optical system of the anterior segment photographing apparatus.

FIG. 2 is a perspective view of an optical system of the present apparatus. FIG. 3 is a side view of the configuration of the optical system of the present apparatus (the present optical system).

The present optical system is broadly divided into the slit illuminating optical system 20, the imaging optical system 30, a fixation target illuminating optical system 40, an alignment illuminating optical system 50, a working distance detecting optical system 60 (60a and 60b), and an anterior segment front imaging optical system 90.

The slit illuminating optical system 20 projects slit light on the anterior segment of the examinee's eye. The imaging optical system 30 includes an imaging optical axis inclined with respect to a slit projection optical axis. The imaging optical system 30 has the imaging lens 33 and the imaging device 35, which are arranged based on the Scheimpflug principle. The working distance detecting optical system 60 detects an alignment state of the measuring unit 8 in the working distance (Z) direction with respect to the examinee's eye. The anterior segment front imaging optical system 90 captures an anterior segment front image. Moreover, a light source that illuminates an anterior segment Ea with infrared light is arranged outside the detecting optical system 60. The present optical system is built in the measuring unit 8.

<Slit Illuminating Optical System>

The slit illuminating optical system 20 (see FIG. 3) includes the light source 21, a condenser lens 22, the slit plate 23, a total reflection mirror 25, the projection lens 26, and a dichroic mirror 24. The dichroic mirror 24 is an optical member having a characteristic that reflects slit light while allowing the other light to pass therethrough. The light source 21 emits light (blue light) with a center wavelength of approximately 470 nm and the wavelength range from approximately 460 to 490 nm. The slit plate 23 is arranged at a position substantially conjugated with the anterior segment (e.g., the vicinity of the corneal apex).

A light flux from the light source 21 is condensed by the condenser lens 22, and irradiates the slit plate 23. The light flux becomes a narrow slit-shaped light flux by the slit plate 23. The light flux is reflected by the total reflection mirror 25 and condensed by the projection lens 26. The light flux is subsequently reflected by the dichroic minor 24 and projected on the eye E as slit light. Consequently, a cross section of the optical media (such as cornea, anterior chamber, and crystalline lens) of the anterior segment of the examinee's eye is illuminated by the slight light.

<Slit Cross-Section Imaging Optical System>

The imaging optical system 30 captures an anterior segment cross-sectional image based on the Scheimpflug principle. The imaging optical system 30 includes a filter 32, the imaging lens 33, the cylindrical lens 38, the second deviation angle prism 37, a mirror 34, the first optical member 36, and the imaging device 35 (see FIG. 3).

The imaging lens 33, the mirror 34, and the first optical member 36 guide to the imaging device 35 reflected light formed by the slight light formed by the slit illuminating optical system 20 being reflected by the anterior segment. The filter 32 allows light (blue light) used for capturing an anterior segment cross-sectional image to pass therethrough while blocking the other light. The filter 32 is arranged forward of the lens 33 (on the eye E side).

The imaging optical system 30 is arranged such that its optical axis (imaging optical axis) intersects with the optical axis of the illuminating optical system 20 at a predetermined angle. In the imaging optical system 30, a light section of a projected image obtained by the illuminating optical system 20, the lens system including a cornea Ec (the cornea and the imaging lens 33), and the imaging surface of the imaging device 35 are arranged to substantially satisfy a Scheimpflug relationship.

The first optical member 36 shifts the angle of an image plane with respect to the optical axis L2 by 10 degrees or more to bring the direction of the image plane close to the perpendicular to the imaging optical axis L2. The light from the slit cross-section of the anterior segment passes through the filter 32 and then converged by the imaging lens 33. The condensed light is then reflected by the mirror 34 through the cylindrical lens 38 and the second deviation angle prism 37. The light reflected by the mirror 34 is incident on the imaging device 35 via the first optical member 36.

As illustrated in FIG. 4, a principal ray B1 is a principal ray of light from a front end of the slit cross-section SL. A principal ray B2 is a principal ray of light from a center position of the slit cross-section SSL. A principal ray B3 is a principal ray of light from a rear end of the slit cross-section SL. Image forming points F1 to F3 are image forming points of light forming the principal rays B1 to B3. A plane (or line) including the image forming points F1, F2, and F3 forms the image plane FF. The imaging surface of the imaging device 35 is arranged at the image plane FF and, accordingly, the light of the principal rays forms an image on the imaging device 35. In reality, the light from the front end to the rear end of the slit cross-section SL is incident on the imaging device 35. The principal rays B1 to B3 are refracted by the first optical member 36. Consequently, the angle of the image plane FF is shifted to bring the direction of the image plane FF with respect to the optical axis L2 close to the perpendicular.

Consequently, the incidence angles (imaging incidence angles) θ of the principal rays B1 to B3 with respect to the imaging device 35 are reduced. Therefore, a light receiving device that is formed on the imaging surface of the imaging device 35 and that corresponds to each pixel receives a large amount of light from the slit cross-section. Consequently, in the present apparatus, even if the exposure time and/or the amount of illuminating light is short and/or small, an anterior segment cross-sectional image having excellent contrast can be acquired.

The light from the slit cross-section SL is reflected by the mirror 34 and, accordingly, the position of the image plane FF is changed. The principal rays B1 to B3 are specularly reflected here by the mirror 34. Hence, in theory, the light from the slit cross-section SL being reflected by the mirror 34 does not change the angle of the image plane FF with respect to the imaging optical axis L2.

In the present apparatus, the cylindrical lens 38 and the second deviation angle prism 37 correct an aberration caused by the first optical member 36. Hence, in the present apparatus, a cross-sectional image having excellent contrast and little aberration can be acquired.

<Fixation Target Illuminating Optical System>

The fixation target illuminating optical system 40 includes a visible light source (e.g., an LED) 41 and a relay lens 42. Light emitted from the light source 41 is projected on the eye E via the relay lens 42, a dichroic mirror 92, a correction optical member 91, the dichroic mirror 24, and an opening portion 66b.

<Alignment Target Illuminating Optical System>

The alignment target illuminating optical system 50 includes a near-infrared light source 51 for alignment, a projection lens 52, a polarizing beam splitter 53, and the dichroic mirror 92. Alignment light emitted from the light source 51 is turned into a parallel light flux by the projection lens 52, and then reflected by the polarizing beam splitter 53. The alignment light is subsequently reflected by the dichroic mirror 92 and heads for the eye E along the optical axis L1. The alignment light is used to project an alignment target on the cornea Ec. The target projected on the cornea (refer to B in FIG. 6) is used for alignment (e.g., automatic alignment, alignment detection, or manual alignment) between the eye E and the measuring unit 8 in the X and Y directions.

<Working Distance Detecting Optical System>

The detecting optical system 60 includes a light projecting optical system (target illuminating optical system) 60a, and a light receiving optical system 60b. The light projecting optical system 60a projects the alignment light for Z detection on the cornea Ec of the examinee's eye from the oblique direction. The light receiving optical system 60b receives the alignment light from the light projecting optical system 60a from the oblique direction, using the light receiving device.

The light projecting optical system 60a includes an infrared light source 61, a reflection prism 62, and a projection lens 63. The light projecting optical system 60a projects infrared light being a target for Z detection on the cornea Ec from the oblique direction. The infrared light source 61 of the light projecting optical system 60a emits infrared light with a wavelength different from that of the light source 51 of the illuminating optical system 50.

The light receiving optical system 60b includes a position sensitive detector (e.g., a line CCD) 69, a reflection prism 68, and a light receiving lens 67. The light receiving optical system 60b detects a target image formed on the cornea Ec by the light projecting optical system 60a. In other words, the light receiving optical system 60b receives the infrared light from the light source 61 that has been reflected by the cornea Ec. The light projecting optical system 60a and the light receiving optical system 60b are arranged in the up and down direction for convenience of description. However, in reality, the line linking them is inclined at a predetermined angle (e.g., 25°) with respect to the horizontal direction. Moreover, they are arranged to be symmetrical about the optical axis L1.

<Anterior Segment Front Imaging Optical System>

The anterior segment front imaging optical system 90 includes the dichroic mirror 92, the polarizing beam splitter 53, a field lens 94, a planar mirror 95, a planar mirror 96, a filter 97, an imaging lens 98, and an imaging device 99. The anterior segment front imaging optical system 90 is used to capture an anterior segment front image of the examinee's eye.

The correction optical member (e.g., a prism) 91 is provided between the dichroic minor 24 and the dichroic minor 92. The correction optical member 91 corrects the displacement of an optical axis caused by the rotation of the dichroic minor 24. The correction optical member 91 has substantially the same thickness and substantially the same refractive index as the dichroic minor 24. The correction optical member 91 is arranged to be symmetrical about the optical axis L1 with the dichroic minor 24. In other words, the correction optical member 91 is arranged to correct the displacement of the optical axis caused by the rotation of the dichroic minor 24.

Moreover, the present apparatus includes the rotation drive mechanism 100 (rotation means). The rotation drive mechanism 100 rotates and moves the slit illuminating optical system 20 and the imaging optical system 30 around the slit projecting optical axis L1.

Next, a description will be given of a control system. A controller 80 controls the entire apparatus and calculates a measurement result. The controller 80 is connected to the light source 21, the light source 41, the light source 51, the light source 61, the drive mechanism 17, the drive unit 101, a sensor 111, the imaging device 35, the position sensitive detector 69, the imaging device 99, an illuminating optical system 45, the monitor 70, a memory 86, and the like. Moreover, the controller 80 is connected to the operating unit 85 for an examiner to perform various input operations. A software program for performing various control programs and various computation operations, and the like are stored in the memory 86. Moreover, stored in the memory 86 is a software program for obtaining a three-dimensional position of a predetermined anterior segment tissue based on anterior segment cross-sectional images photographed at a plurality of rotation angles and their rotation angle information upon photographing, and measuring the shape of the anterior segment tissue.

Moreover, the operating unit 85 may include, as an operation input unit, a general interface such as a mouse, or a touchscreen.

The controller 80 sets a photographing mode based on a switching signal from a mode selection switch 85a. In a first mode, the controller 80 photographs anterior segment cross-sectional images at a plurality of rotation angles by the slit illuminating optical system 20 and the imaging optical system 30. The controller 80 measures the shape of the anterior segment tissue based on these images.

Figure 6:
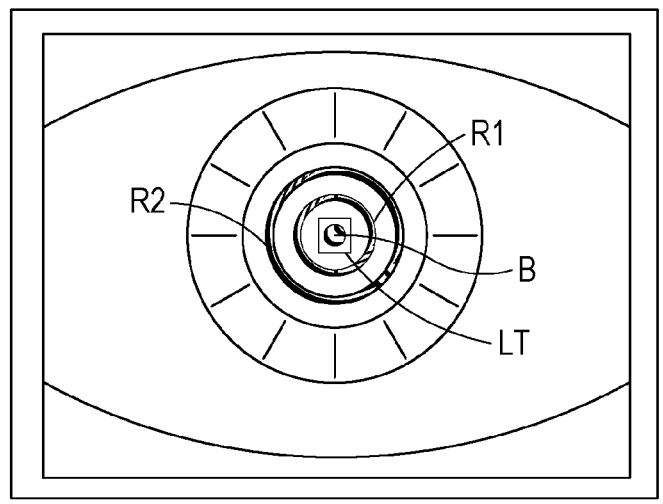
FIG. 6 is a diagram illustrating an example of an anterior segment observation screen of the anterior segment photographing apparatus.

A description will be given of the operation of the present apparatus including the above configuration. Firstly, a case where the photographing mode is the first mode will be described. The examiner moves the measuring unit 8 in the X, Y, and Z directions using the joy stick 12 while watching the alignment state of the examinee's eye displayed on the monitor 70 (see FIG. 6). At this point, the examiner causes the examinee (the examinee's eye E) to fixate on an unillustrated fixation target. Moreover, a reticle LT illustrated in FIG. 6 is a mark electronically displayed as an alignment reference.

The measuring unit 8 is moved as described above, and a target image B is detected. The controller 80 subsequently detects the coordinate position of the target image B as a substantial corneal apex based on an imaging signal from the imaging device 99. The controller 80 detects misalignment (including the direction of displacement and the amount of displacement (the amount of deviation)) in the X and Y directions, based on the detection result. The controller 80 then controls the drive mechanism (drive unit) 17, and moves the measuring unit 8 in the X and Y directions such that the misalignment in the X and Y directions falls within a predetermined alignment tolerance.

Moreover, the controller 80 detects misalignment (including the direction of displacement and the amount of displacement (the amount of deviation)) in the Z direction based on a light receiving signal from the position sensitive detector 69. The controller 80 then controls the drive mechanism 17, and moves the measuring unit 8 in the Z direction such that the misalignment in the Z direction falls within a predetermined alignment tolerance.

When the misalignments in the X, Y, and Z directions satisfy the condition of completion of alignment with the above-mentioned alignment operations, the controller 80 judges that the X, Y, and Z directions are aligned, respectively, and emits a trigger signal for the start of measurement.

<Photographing of Cross-Sectional Image>

If the trigger signal for the start of measurement is emitted, the controller 80 lights up the light source 21. Furthermore, the controller 80 drives the drive unit 101, and rotates a rotation unit 200 (the correction optical member 91, the slit illuminating optical system 20, and the imaging optical system 30) around the optical axis L1. With the lighting of the light source 21, optical sectioning is performed on the anterior segment by the slit light. The scattered light from the anterior segment, on which optical sectioning has been performed by the slit light, heads for the imaging optical system 30. As a consequence, a cross-sectional image is photographed by the imaging device 35. At this point, the controller 80 stores in the memory 86 a photographing image outputted from the imaging device 35 at every predetermined rotation angle while associating the photographing image with the number of pulses of the drive unit 101. Moreover, the controller 80 stores also information on a photographing angle while associating the information with the photographing image. During rotation photographing, the photographing light amount of the light source 21 is controlled to be substantially constant.

Moreover, during rotation photographing, the controller 80 detects an alignment state in the Z direction using the detecting optical system 60. The controller 80 controls the drive mechanism 17 based on the detection result to correct the displacement of the eye E during photographing. Consequently, also during rotation photographing, Z tracking (alignment in the Z direction) is performed at every predetermined rotation angle. Naturally, the controller 80 may drive the drive mechanism 17 based on the alignment detection results in the X and Y directions to perform X-Y tracking (alignment in the X and Y directions). The controller 80 may correct the displacement (misalignment) of each cross-sectional image by image processing based on the alignment detection result at every rotation angle.

The rotation unit 200 is rotated half a round to obtain a full rounds worth of a photographing image. Therefore, the number of photographing images is preferably 18 (photographing at every rotation angle of 10 degrees) or more. The number of photographing images is more preferably 36 (photographing at every rotation angle of five degrees) or more. In the example, if the width of the slit light is set to 80 μm to carry out as accurate a stereo analysis as possible, photographing is carried out at every rotation angle of 2.25 degrees. Consequently, 80 images are photographed, and stored automatically in the memory 86. The rotation angle may be fixed. Moreover, a configuration where the examiner can set the rotation angle arbitrarily is preferable.

The slit illuminating optical system 20 and the imaging optical system 30 are placed at an initial rotation angle (e.g., 0 degree position) before photographing. Whether the illuminating optical system 20 and the imaging optical system 30 are at the initial position is detected by the sensor 111. A return to the initial position is performed on startup of the present apparatus, or when an unillustrated reset switch of the operating unit is pressed. Moreover, when three-dimensional photographing ends, the drive unit 101 is driven, and the illuminating optical system 20 and the imaging optical system 30 are arranged at the initial position.

When photographing is complete, the controller 80 calls up all the photographing images stored in the memory 86 and the rotation angle information of the photographing images. The controller 80 uses the software program to make the photographing images three-dimensional (three-dimensional reconstruction) and stores them in the memory 86.

After the measurement ends as described above, the controller 80 calculates from the anterior segment cross-sectional images the measurement values of tissues such as the curvature of the front surface of the cornea, the curvature of the back surface of the cornea, corneal thickness, the curvature of the anterior surface of the crystalline lens, the curvature of the posterior surface of the cornea, crystalline lens thickness, and anterior chamber depth. These measurement results are stored in the memory 86 and outputted to the monitor 70.

As described above, in the present apparatus, a slit projecting system and a Scheimpflug camera rotate. At each rotation position, an anterior segment cross-sectional image is photographed. Furthermore, the present apparatus includes a Z alignment detecting system. Consequently, the present apparatus can carry out measurements on the anterior segment accurately. Moreover, in the present apparatus, alignment in the Z direction is detected also during photographing of a cross-sectional image. Consequently, the displacement between cross-sectional images can be corrected. Tracking may be performed while the Scheimpflug camera is being rotated. Moreover, upon tracking, the rotation and movement of the Scheimpflug camera may be temporarily stopped. In this case, after completion of tracking, photographing may be resumed.

Moreover, in the example, the imaging optical system 30 includes the first optical member 36. Consequently, only a short exposure time is necessary. Hence, photographing time can be reduced. Therefore, even when cross-sectional images at a plurality of rotation positions are continuously acquired as described above, the total photographing time can be reduced.

The present apparatus may have a configuration, in an imaging optical system having an imaging optical axis that is inclined with respect to and intersects with an optical axis of an illuminating optical system, to shift an image plane by the imaging optical system to the perpendicular side with respect to the imaging optical axis. Consequently, a captured image having excellent contrast, for example can be obtained. Another object is that image acquisition time can be reduced.

The first optical member 36 may refract a principal ray of light from the slit cross-section SL, including a principal ray of light on the imaging optical axis L2. Consequently, the angle of the image plane FF with respect to the optical axis L2 is shifted to the perpendicular side. The imaging surface of the imaging device 35 is arranged at the image plane FF shifted by the first optical member 36. Consequently, a cross-sectional image that is in focus with respect to a depth direction is captured.

Moreover, the ophthalmologic photographing apparatus according to the embodiment may be the following first to tenth ophthalmologic photographing apparatuses. The first ophthalmologic photographing apparatus includes an illuminating optical system (20) that irradiates an examinee's eye with illuminating light, an imaging optical system (30) having an imaging device (35) that receives a reflected light flux from the eye, and having an imaging optical axis inclined with respect to an optical axis of the illuminating optical system, and a first optical member (36) for reducing the incidence angle of a principal ray of the reflected light flux with respect to an imaging surface of the imaging device.

In the first ophthalmologic photographing apparatus, the second ophthalmologic photographing apparatus includes an aberration correction member (37, 38) for correcting an aberration caused by the first optical member. In the first or second ophthalmologic photographing apparatus, the third ophthalmologic photographing apparatus is provided with the illuminating optical system and the imaging optical system to photograph anterior segment cross-sectional images, and further includes drive means (100) for photographing the anterior segment cross-sectional images at a plurality of positions. In any one of the first to third ophthalmologic photographing apparatuses, the forth ophthalmologic photographing apparatus has the first optical member that is an optical member for refracting the reflected light flux from the eye and refracting the imaging optical axis.

In any one of the first to fourth ophthalmologic photographing apparatuses, the fifth ophthalmologic photographing apparatus has the first optical member that is either a deviation angle prism or a Fresnel prism. In the first to fifth ophthalmologic photographing apparatuses, the sixth ophthalmologic photographing apparatus has the aberration correction member that is at least any of a deviation angle prism, a Fresnel prism, and a cylindrical lens. In any one of the first to sixth ophthalmologic photographing apparatuses, the seventh ophthalmologic photographing apparatus has the imaging device that is arranged such that the incidence angle of a principal ray with respect to the imaging surface is 20° or less. In any one of the first to seventh ophthalmologic photographing apparatuses, the eighth ophthalmologic photographing apparatus has the imaging optical system that is based on a configuration where the Scheimpflug principle is used for its arrangement.

In any one of the first to eighth ophthalmologic photographing apparatuses, the ninth ophthalmologic photographing apparatus has the first optical member arranged on an optical path of the imaging optical system. In any one of the first to eighth ophthalmologic photographing apparatuses, the tenth ophthalmologic photographing apparatus has the imaging optical system further having a lens system (33), and has the first optical member arranged between the lens system and the imaging device.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmologic photographing apparatus comprising:
   an illuminating optical system for irradiating an examinee's eye with illuminating light;
   an imaging optical system including an imaging device for receiving a reflected light flux from the eye, an optical axis of the reflected light flux from the eye being inclined with respect to an optical axis of the illuminating light into the eye; and
   a first optical member for reducing an imaging incidence angle, the imaging incidence angle being defined as an angle between a normal direction of an imaging surface of the imaging device and an optical axis of the reflected light flux when the reflected light flux is incident on the imaging device,
   wherein the imaging surface of the imaging device is shifted, due to the first optical member, from a position following a Scheimpflug principle as a function of a reduction in the imaging incidence angle.

2. The ophthalmologic photographing apparatus according to claim 1, further comprising an aberration correction member for correcting an aberration caused by the first optical member.

3. The ophthalmologic photographing apparatus according to claim 1, further comprising a drive mechanism for moving the illuminating optical system and the imaging optical system to photograph anterior segment cross-sectional images at a plurality of positions, wherein the illuminating optical system and the imaging optical system are provided to photograph the anterior segment cross-sectional images.

4. The ophthalmologic photographing apparatus according to claim 1, wherein the first optical member refracts the reflected light flux and the imaging optical axis.

5. The ophthalmologic photographing apparatus according to claim 1, wherein the first optical member is any of a deviation angle prism and a Fresnel prism.

6. The ophthalmologic photographing apparatus according to claim 2, wherein the aberration correction member is at least any of a deviation angle prism, a Fresnel prism, and a cylindrical lens.

7. The ophthalmologic photographing apparatus according to claim 1, wherein the imaging device is arranged to obtain the imaging incidence angle of 20° or less.

8. The ophthalmologic photographing apparatus according to claim 1, wherein the first optical member is arranged on an optical path of the imaging optical system.

9. The ophthalmologic photographing apparatus according to claim 8, wherein
   the imaging optical system further includes an imaging lens for converging the reflected light flux, and
   the first optical member is arranged between the imaging lens and the imaging device.

10. The ophthalmologic photographing apparatus according to claim 1, wherein the illuminating light is a slit light, and the reflected light flux received by the imaging device from the eye is the reflected slit light.

11. The ophthalmologic photographing apparatus according to claim 1, wherein the illuminating light being irradiated to the eye does not share an optical axis with the reflected light flux from the eye.

12. The ophthalmologic photographing apparatus according to claim 1, wherein the illuminating optical system irradiates the eye with the illuminating light from an oblique direction with respect to a cornea, and the imaging optical system receives the reflected light flux that is specularly reflected by the cornea of the eye.

13. The ophthalmologic photographing apparatus according to claim 1, wherein an amount of the reflected light flux incident on the imaging surface of the imaging device is increased compared to an amount of the reflected light flux incident by following the Scheimpflug principle.

14. The ophthalmologic photographing apparatus according to claim 1, wherein the illuminating light into the eye does not share an optical axis with the reflected light flux from the eye; and
   the first optical member is provided between the eye and the imaging device and configured to refract the reflected light flux from the eye such that the imaging incidence angle is reduced.

15. The ophthalmologic photographing apparatus according to claim 1, wherein the illuminating light into the eye does not share an optical axis with the reflected light flux from the eye; and
   the first optical member is provided between the eye and the imaging device and configured to refract the reflected light flux from the eye such that the imaging incidence angle is reduced as compared to an imaging incidence angle when the imaging device is arranged based on the Scheimpflug principle.

16. The ophthalmologic photographing apparatus according to claim 1, wherein the imaging surface of the imaging device is shifted due to the first optical member such that the imaging incidence angle is reduced as compared to an imaging incidence angle when the imaging device is arranged based on the Scheimpflug principle.

* * * * *